United States Patent [19]

Glintz

[11] 4,248,216
[45] Feb. 3, 1981

[54] DISPOSABLE STRETCHER CARE SHEET

[76] Inventor: Georgia E. Glintz, 2909 University Ave., Des Moines, Iowa 50311

[21] Appl. No.: 39,667

[22] Filed: May 16, 1979

[51] Int. Cl.³ .............................................. A61F 13/00
[52] U.S. Cl. .................................. 128/132 D; 5/82 R
[58] Field of Search .............. 128/132 R, 132 D, 292, 128/760; 4/177 R, 112, 113; 5/82 R

[56] References Cited

U.S. PATENT DOCUMENTS

| | | | |
|---|---|---|---|
| D. 25,728 | 6/1896 | Searby | 4/112 UX |
| 330,548 | 11/1885 | Beal | 4/112 |
| 443,593 | 12/1890 | Dugot | 4/112 |
| 763,304 | 6/1904 | Meinecke et al. | 128/292 |
| 1,011,114 | 12/1911 | Button | 4/177 |
| 2,279,694 | 4/1942 | Martinson | 5/82 |
| 2,551,673 | 5/1951 | Hassolguist | 4/177 |
| 3,927,667 | 12/1975 | Criddle et al. | 128/132 D |

*Primary Examiner*—Lawrence W. Trapp

*Attorney, Agent, or Firm*—Clarence A. O'Brien; Harvey B. Jacobson

[57] ABSTRACT

An outwardly opening receptacle constructed of flexible water impervious material. The receptacle includes a bottom and upstanding peripheral sides and is generally ellipsoidal in plan shape. The upstanding peripheral sides include successive reversely foldable upper marginal zones selectively foldable inwardly and outwardly relative to the peripheral sides of the receptacle and the marginal zones taper in width, oppositely, toward the opposite ends of the receptacle. The opposite ends of the receptacle include flexible drain tube portions opening outwardly therefrom and the outer end portions of the drain tube portions include closed reservoir defining end portions. Tie members are carried by the drain tube outer end portions inwardly of the reservoir defining end portions and the drain tube portions are capable of being readily cut by scissors, or the like.

14 Claims, 5 Drawing Figures

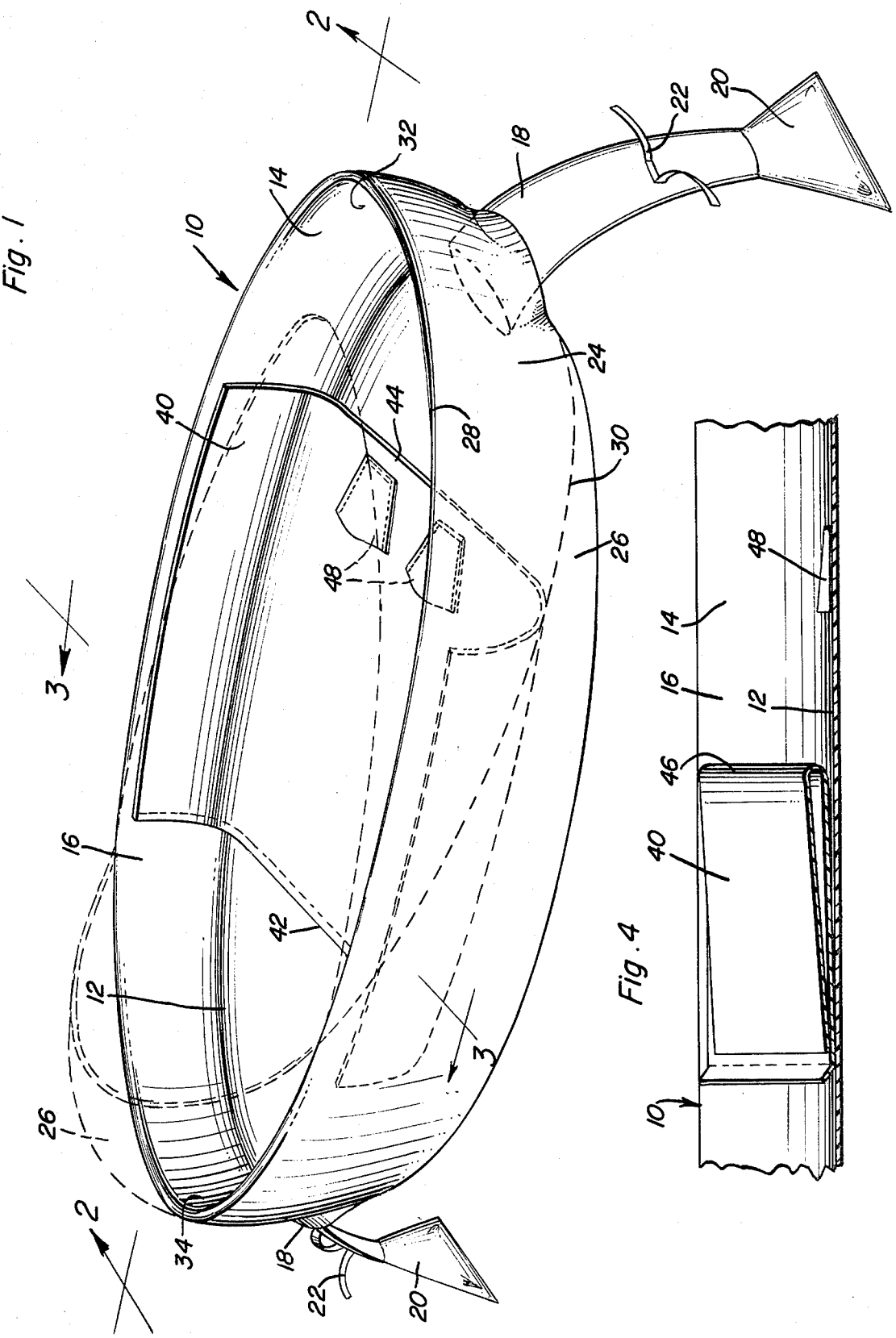

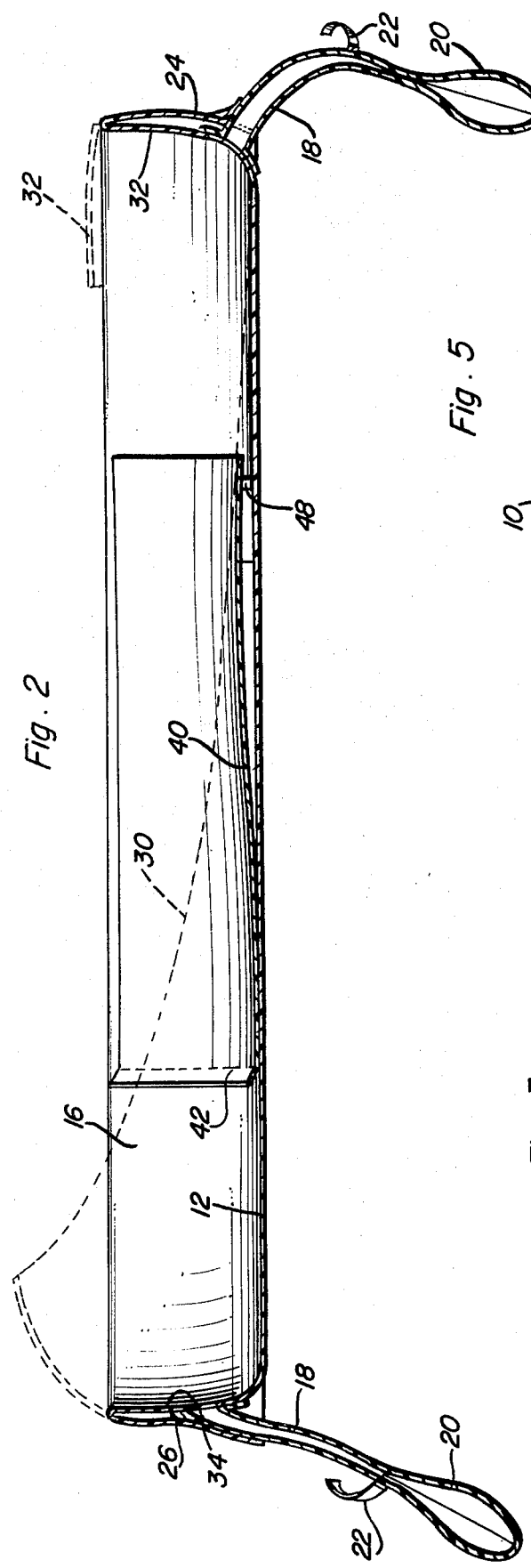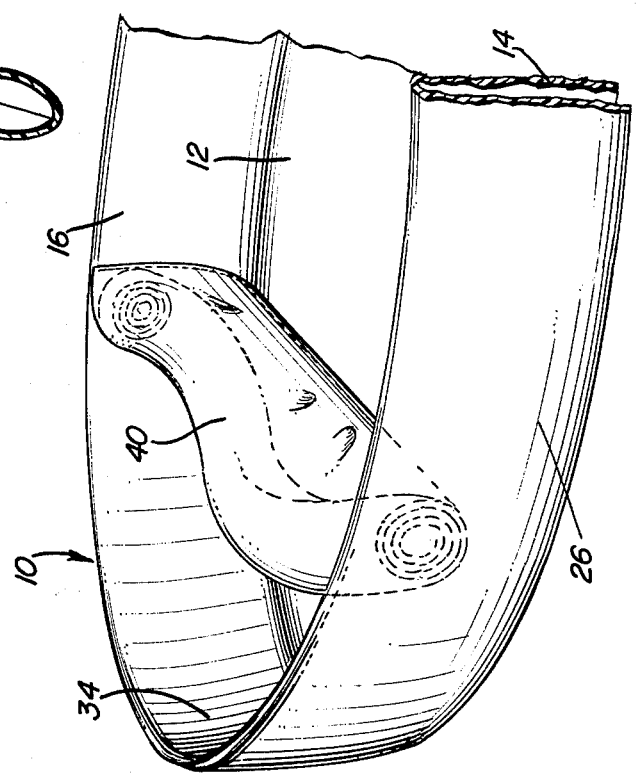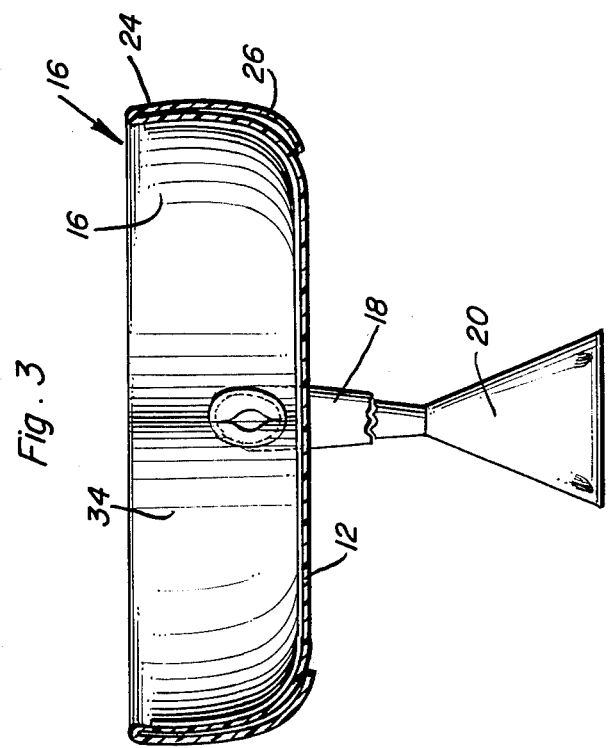

DISPOSABLE STRETCHER CARE SHEET

BACKGROUND OF THE INVENTION

In many instances persons requiring medical care are themselves soiled or must await medical assistance while lying upon unclean surfaces. Accordingly, a need exists for some structure whereby a soiled accident victim, or the like, may be placed within a suitable receptacle for treatment in an emergency room, or the like, in such a manner that the immediate areas of the emergency room are not contaminated. Such a receptacle may also be utilized for accident victims on the roadside awaiting medical care to protect the accident victim therewithin against unclean surfaces upon which the accident victim may be resting.

Such a receptacle may be readily constructed of lightweight water impervious material and may be carried in a compact state and discarded after usage.

Although various forms of sanitary sheets and body coverings and supports have been heretofore provided, such as those disclosed in U.S. Pat. Nos. 590,188, 3,108,293, 3,791,962, 3,791,382, 3,986,505, 4,002,330 and 4,006,017, these previously known structures are not specifically designed for use in containing an accident victim for protection of the victim against contamination from unclean surroundings or for containing an accident victim against contamination of adjacent clean areas.

BRIEF DESCRIPTION OF THE INVENTION

The care sheet of the instant invention defines a shallow upwardly opening receptacle including a bottom and upstanding peripheral sides. In addition, the upper marginal portions of the sides include successive first and second marginal zones reversely selectively foldable inwardly and outwardly relative to the peripheral sides of the receptacle. The marginal zones taper in width, oppositely, toward opposite ends of the receptacle and the opposite ends of the receptacle include flexible drain tube portions opening outwardly therefrom and provided with closed reservoir defining ends which may be tied closed and cut from the remainder of the flexible drain tube portions. The reversely foldable first and second zones may be selectively foldable inwardly over a patient within the receptacle, or outwardly over the side walls of the receptacle for reinforcing the latter.

The main object of this invention is to provide a receptacle in which soiled persons may be contained for protection of adjacent clean areas against contamination and in which patients (accident victims, and the like) may be contained for protection against contamination from unclean surrounding areas.

Another object of this invention is to provide a receptacle in which a soiled patient may be bathed.

A further object of this invention is to provide a receptacle which may be readily stored in a compact folded state.

A further important object of this invention is to provide a receptacle of low cost construction whereby the receptacle may be discarded after use.

A still further object of this invention is to provide a receptacle which may be utilized to collect and trap body fluids draining from a patient therein.

A final object of this invention to be specifically enumerated herein is to provide a receptacle in accordance with the preceding objects and which will conform to conventional forms of manufacture, be of simple construction and easy to use so as to provide a device that will be economically feasible, long lasting and relatively trouble-free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the care sheet;

FIG. 2 is an enlarged fragmentary vertical sectional view taken substantially upon the plane indicated by the section line 2—2 of FIG. 1;

FIG. 3 is an enlarged transverse vertical sectional view taken substantially upon the plane indicated by the section line 3—3 of FIG. 1;

FIG. 4 is an enlarge fragmentary vertical sectional view illustrating the manner in which a transverse partition of the care sheet may be folded; and FIG. 5 is a fragmentary perspective view illustrating the manner in which the transverse partition of the care sheet may be rolled to form a neck cushion and dam about the neck and shoulders of a patient within the sheet.

DETAILED DESCRIPTION OF THE INVENTION

Referring now more specifically to the drawings, the numeral 10 generally designates the care sheet of the instant invention. The care sheet 10 is constructed of flexible waterproof material, such as thin sheet plastic, and includes a bottom 12 and an upstanding peripherally extending side wall 14. The bottom and side wall 14 define a shallow upwardly opening receptacle 16 and it will be noted that the receptacle 16 is ellipsoidal in plan shape including opposite end portions. The opposite end portions of the receptacle 16 include flexible drain tube portions 18 opening outwardly therefrom and the outer ends of the drain tube portions 18 include enlarged closed reservoir defining ends 20. In addition, tie strings 22 are supported from the tube portions 18 and may be tied about the latter for closing the same intermediate the end portions 20 and the receptacle 16. After the tie strings 22 have been tied, the tube portions 18 may be cut with any suitable tool, such as scissors, between the receptacle 16 and tie strings 22 and any fluids collected within the reservoir defining end portions 20 may be carried to a laboratory area for tests to be performed thereon.

The upper marginal portions of the side walls 14 terminate upwardly in successive first and second marginal zones 24 and 26 with a fold line 28 defined between the marginal zone 24 and the side wall 14 and a second fold line 30 defined between the first and second zones 24 and 26. The zones 24 and 26 may be folded, in either direction, along the fold lines 28 and 30 and it will be noted that the zone 24 tapers transversely toward the foot end 32 of the receptacle 16 while the zone 26 tapers transversely toward the head end 34 of the receptacle 16.

As may best be seen from FIG. 1 of the drawings, when the zones 24 and 26 are folded over the interior of the receptacle 16, the zone 24 defines a head and shoulder area receiving hood portion and the zone 26 defines a partial cover over the foot receiving end of the receptacle 16. However, when the zones 24 and 26 are folded over the outer side of the receptacle 16, the transversely wider portions of the zones 24 and 26 reinforce the head and foot ends 34 and 32 of the receptacle 16 from the exterior thereof.

The interior of the receptacle 16 includes a divider panel 40 therein extending across the longitudinal center portion of the bottom wall 12 and upwardly along the inner surface of the longitudinally extending portions of the side wall 14. One marginal portion 42 of the divider panel 40 is sealingly secured to the opposing inner surfaces of the bottom wall 12 and the side wall 14 and the remote marginal portion 44 merely rests upon the bottom wall 12 and loosely engages the inner surfaces of the opposing portions of the side wall 14. The divider panel may be rolled in the manner illustrated in FIG. 4 of the drawings to define a neck and head cushion and may be draped over the adjacent shoulder portions of a patient disposed within the receptacle 16. The divider panel 40, in such a configuration, divides the interior of the receptacle 16 into a small head receiving compartment and a larger torso receiving compartment with communication between those compartments prevented by fluids collected within the bottom of the receptacle 16. Also, the bottom wall 12 of the receptacle 16 includes foot stalls 48 which open toward the head end 34 of the receptacle 16 and in which the feet of a person disposed within the receptacle 16 may be received with the knees of that person in a raised position. The marginal portion 44 of the divider panel 40 overlies the foot stalls 48 when the divider panel 40 is in its unrolled condition illustrated in FIG. 1.

The divider panel 40 may be initially folded in the manner illustrated as at 46 in FIG. 4 before being rolled into the rolled condition thereof illustrated in FIG. 5.

It will, of course, be noted that the care sheet 16 may have all of its components constructed of relatively thin, flexible and lightweight plastic material. Thus, the care sheet 10 may be readily stored in a compact folded state. Further, the expense of producing and marketing the care sheet 10 is held at a minimum and, accordingly, the care sheet 10 may be disposed of after its initial use at a minimum of cost.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A patient care sheet for containing a patient, said care sheet being flexible and constructed of water impervious material and defining an upwardly opening receptacle including a bottom wall and upstanding peripheral sides, said receptacle being generally ellipsoidal in plan shape, said upstanding peripheral sides including successive first and second marginal zones selectively foldable inwardly and outwardly relative to the peripheral sides of said receptacle, said marginal zones tapering in width, oppositely, toward opposite ends of said receptable, the opposite ends of said receptacle including flexible drain tube portions opening outwardly therefrom.

2. The combination of claim 1 wherein the outer end portions of said drain tube portions include closed reservoir defining end portions.

3. The combination of claim 2 wherein said tube portions, inwardly of said reservoir defining end portions, include tie members attached thereto for tieing closed the tube portions inwardly of said reservoir defining end portions, said material being capable of being readily cut by scissors, whereby the tied closed reservoir defining end portions may be cut from the remaining tube portions.

4. The combination of claim 1 wherein said ellipsoidal receptacle defines head and end portions thereof, the bottom wall of said receptacle including foot stalls on the end portion thereof corresponding to the foot end of said receptacle and opening toward the head end of said receptacle.

5. The combination of claim 1 including an elongated divider panel extending transversely of the inner portion of said receptacle across the central area of the bottom wall thereof and including opposite ends projecting upwardly along the inner surfaces of said sides, one longitudinal marginal edge of said divider panel being sealingly secured to the underlying inner surfaces of said bottom wall and opposite side wall portions.

6. The combination of claim 5 wherein said divider panel is rollable, from the other longitudinal marginal edge portion thereof toward said one longitudinal edge portion thereof in order to form a neck and head supported pillow in one end of said receptacle.

7. The combination of claim 6 wherein said bottom wall includes foot stalls carried by the upper surface thereof in the end portion of said receptacle remote from said one end portion and opening toward said one end portion.

8. The combination of claim 6 wherein said bottom wall includes foot stalls carried by the upper surface thereof in the end portion of said receptacle remote from said one end portion and opening toward said one end portion and wherein the outer end portions of said drain tube portions include closed reservoir defining end portions.

9. The combination of claim 8 wherein said tube portions, inwardly of said reservoir defining end portions, include tie members attached thereto for tieing closed the tube portions inwardly of said reservoir defining end portions, said material being capable of being readily cut by scissors, whereby the tied closed reservoir defining end portions may be cut from the remaining tube portions.

10. A patient care sheet for wholly containing a patient, said care sheet being flexible and constructed of water impervious material and defining an upwardly opening elongated receptacle including a bottom wall and upstanding peripheral sides, the opposite ends of said receptacle including flexible drain tube portions opening outwardly therefrom, an elongated divider panel extending transversely of the inner portion of said receptacle across and overlying the central area of the bottom wall thereof and including opposite ends projecting upwardly along the inner surfaces of said sides, one longitudinal marginal edge of said divider panel being sealingly secured to the underlying inner surfaces of said bottom wall and opposite side wall portions, said divider panel being rollable, from the other longitudinal marginal edge portion thereof toward said one longitudinal edge portion thereof in order to form a neck and head supportive pillow in said one end of said receptacle.

11. The combination of claim 10 wherein the outer end portions of said flexible drain tube portions include closed reservoir defining end portions.

12. The combination of claim 11 wherein said tube portions, inwardly of said reservoir defining end portions, include tie members attached thereto for tieing closed said tube portions inwardly of said reservoir defining end portions, said material being capable of being readily cut by scissors, whereby the tied closed reservoir defining end portions may be cut from the remaining tube portions.

13. The combination of claim 5 wherein said divider panel includes foot stalls supported from the upper surface thereof adjacent the other longitudinal edge of said divider panel and opening toward said one longitudinal edge thereof.

14. The combination of claim 10 wherein said divider panel includes foot stalls supported from the upper surface thereof adjacent the other longitudinal edge of said divider panel and opening toward said one longitudinal edge thereof.

* * * * *